United States Patent [19]
Crowley

[11] Patent Number: 4,776,111
[45] Date of Patent: Oct. 11, 1988

[54] FOOTWEAR STABILIZER

[76] Inventor: Kevin J. Crowley, Pickpocket Rd., Brentwood, N.H. 03833

[21] Appl. No.: 900,740

[22] Filed: Aug. 27, 1986

[51] Int. Cl.⁴ .......................... A43B 7/20; A43B 7/14; A43B 5/00
[52] U.S. Cl. .......................................... 36/89; 36/50; 36/69; 36/114
[58] Field of Search ................. 36/89, 114, 50, 115, 36/117-121, 132, 69, 68; 128/166, 80 H

[56] References Cited

U.S. PATENT DOCUMENTS

| | | | |
|---|---|---|---|
| 660,885 | 10/1900 | Brauer et al. | 128/166 |
| 1,084,197 | 1/1914 | Collis | 128/166 |
| 2,444,428 | 7/1948 | Carrier | 36/89 X |
| 3,494,054 | 2/1970 | Lange | 36/120 |
| 3,538,627 | 11/1970 | Labat-Camy | 36/120 |
| 3,636,642 | 1/1972 | Walther | 36/120 |
| 4,459,765 | 7/1984 | Power | 36/69 X |
| 4,470,205 | 9/1984 | Olivieri | 36/114 |
| 4,571,856 | 2/1986 | Lin et al. | 36/89 |
| 4,625,435 | 12/1986 | Ueda | 36/68 |
| 4,676,011 | 6/1987 | O'Rourke et al. | 36/89 |

FOREIGN PATENT DOCUMENTS

| | | | |
|---|---|---|---|
| 2527427 | 12/1983 | France | 36/89 |
| 2606800 | 8/1977 | Fed. Rep. of Germany | 36/89 |

Primary Examiner—James Kee Chi

[57] ABSTRACT

A footwear stabilizer for athletic shoes comprising a sole, an upper attached to the sole and having an opening, and a tongue to complete the opening. Exterior stabilizer means comprising a collar compliant about the ankle and stiff vertically, and a pair of stiffening elements attached to and pivoted about pivot points on opposite sides of the foot below the malleoli, each element extending upwards to join the collar. The collar is tightened about the ankle and joined in front by the shoelaces which pass through eyelets or grommets and also through registered eyelets of the upper and grommets of the collar. The shoe also has a stiff support and a support plate protecting the heel and achilles tendon.

8 Claims, 2 Drawing Sheets

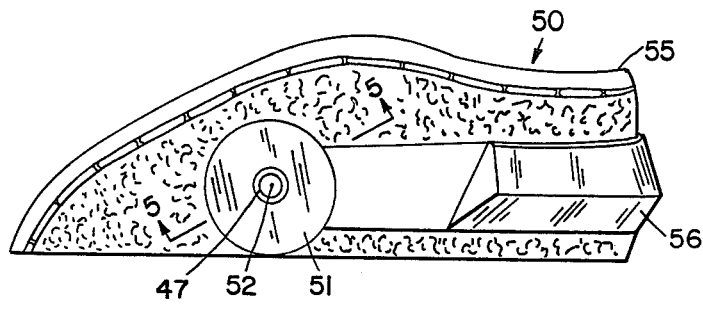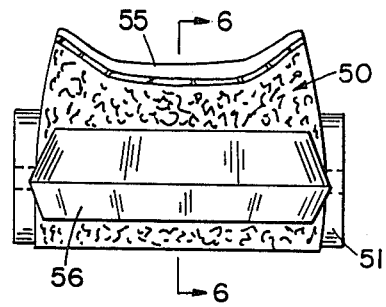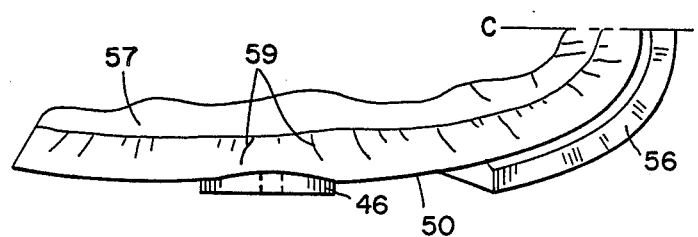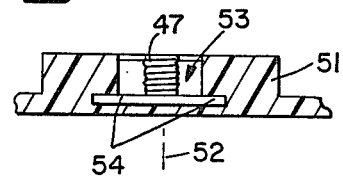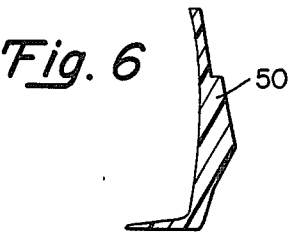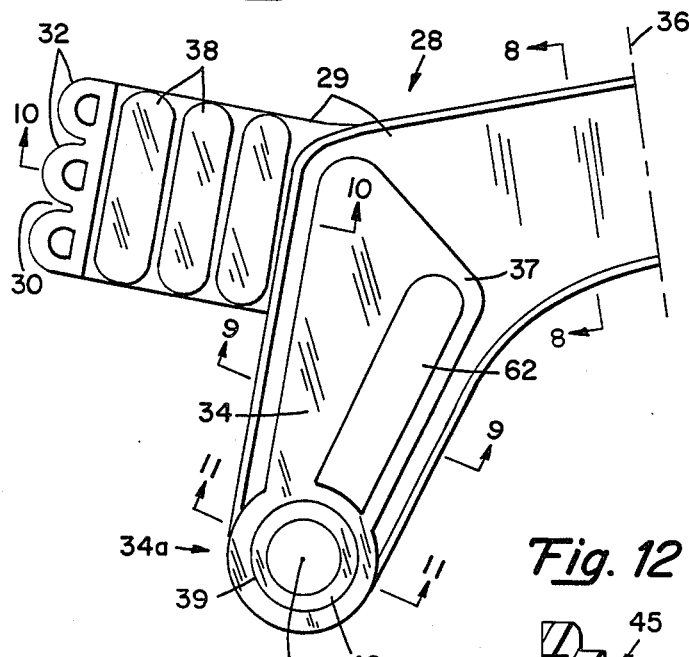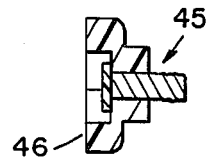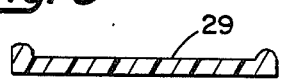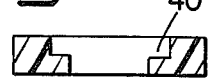

ary, July 11, 25

FOOTWEAR STABILIZER

FIELD OF THE INVENTION

The invention is related to support structures for shoes, and more particularly to stabilizers for footwear.

BACKGROUND OF THE INVENTION

Many workers have endeavored to design footwear that resists injury to the foot, and especially spraining of the ankle resulting from pronation. For example, U.S. Pat. No. 1,205,206 to Hofmeister, Nov. 21, 1916 for "Foot Protector" proposes an ankle support and an arch support on each side of, and inside of, the shoe pivotally connected to the ankle support to resist such sprains as may occur in the football field. U.S. Pat. No. 1,441,677 to Golden, Jan. 9, 1923 for "Braced Shoe" proposes a swinging side brace vertically extended and a forward brace horizonally extended, swinging in a limited manner around a common pivot on one side only of the shoe. U.S. Pat. No. 1,546,551 to Petri on July 2, 1965 for "Ankle Brace" suggests that an encircling spring metal braces tightly buckled and pivoting above the malleoli to protect the ankle of a skater.

Also, U.S. Pat. No. 2,165,879 to Wilkinson, July 11, 1939 for "Ankle Support" describes a laced canvas and ribbed support which encircles the heel and rear of the foot and is laced in front about the ankle inside the shoe to lend support to the ankle. U.S. Pat. No. 2,444,428 to Carrier, July 6, 1948, for "Shoe For Sports And The Like" proposes relatively independent upper and lower parts which are separately laced, the upper part being laced both front and back. The Carrier patent also describes a lateral shell of thick and rigid leather on each side to encase the ankle and affixed to an upper part pivotally fixed to a lug below the outside by a rivet. U.S. Pat. No. 2,972,822 to Tanner, Feb. 28, 1961, for "Ankle Support Device" describes a device worn over the wear ing boot. This device includes a tongue attached to an ankle strap, or to the ankle portion of the boot, and at the lower device part to a heel plate. Between these connections and about the ankle is a pair of cooperatting ring portions encircling the ankle (malleoli) allowing rotation of the upper part about the lateral axis of the ankle bone by the cooperating ring ceters, but resisting rotation about a longitudinal axis.

U.S. Pat. No. 3,613,271 to Geller for "Reshapeable Boot or Shoe and Method of Reshaping" describes an elastic support anchored laterally to the wearer's shoe near the sole below the ankle and connected laterally above the ankle. This elastic support biases the foot against "turning of the ankle" by tending to prevent stretching of the outer ankle tendons, being under tension when such stretching begins. U.S. Pat. No. 3,970,083 to Carrigan, et al, July 10, 1976, for "Ankle Support" suggests a pliable single piece jacket fitted and laced inside the shoe about foot and ankle by conventional lacing. The jacket encloses on opposite sides elongated stiffening strips in a generally inverted T shape, the inverted base of the T being generally vertically along the leg, the intersection of the T being below the ankle. These strips are aligned generally with the key natural ligaments of the ankle, especially the lateral side of the ankle, whereby the strips reinforce these ligaments.

Further, U.S. Pat. No. 4,441,265 to Burns, et al, Apr. 10, 1984 is intended to inhibit ankle injuries by a "high cut" athletic boot. A band of stretchable material is anchored at the outside of the boot rearwardly over the dorsal surface of the shoe to the inside of the ankle where it is fastened under tension above the ankle. This band is intended to place the foot in a slightly valgus position reducing stress on the major ligaments yet permitting normal pronation and supination of the forefoot and plantar flexion and dorsiflexion of the foot. U.S. Pat. No. 4,523,394 to Lindh, et al, June 18, 1985, for "Ankle Ligament Protective Device" describes a protective device comprising a foot plate from the heel portion over the arch, and ankle sleeve with fastening means and fixed around the ankle portion of the foot, and nonextensible flexible connections arranged to connect the ankle sleeve on both sides of the foot to the foot plate, to prevent sideways overstretching movements. U.S. Pat. No. 4,571,856 to Lin, et al, Feb. 26, 1986, for "Double Laced Athletic Shoe" describes an athletic shoe with a "high topped" upper, laced as usual, and an inner extending from the lateral side of the sole portion of the upper to the medial side portion rearwardly around the ankle to provide support.

SUMMARY OF THE INVENTION

According to the invention, an athletic shoe comprises a sole, an upper having an opening, and a tongue to complete the opening. The shoe has means for closing the opening about the foot, and exterior stabilizer means comprising a collar compliant about the ankle above the malleoli and stiff in the vertical direction, and a pair of stiff elements attached to and pivoted about pivot points on opposite sides of the foot below the malleoli and each extending upwards from the pivot points to join the collar. The collar is tightened and joined at the front by the closing means, preferably a lacing through registering grommets and eyelets in the collar and upper respectively. The collar is also stiffened vertically.

DESCRIPTION OF THE DRAWINGS

The various objects, advantages, and novel features of the invention will be more fully apparent from the following detailed description, when read in connection with the accompanying drawing, in which like characters refer to like parts, and in which:

FIG. 2 is a side view of a portion of the shoe of FIG. 1;

FIG. 3 is a rear view of the portion of FIG. 2;

FIG. 4 is a half of a top view of the shoe of FIG. 3 with the exterior stabilizer means partially removed;

FIG. 5 is a sectional view along the lines 5—5 of FIG. 2;

FIG. 6 is a sectional view along the lines 6—6 of FIG. 3;

FIG. 7 is a half-view of an element of the shoe of FIG. 1 expanded;

FIGS. 8, 9, 10, and 11 are, respectively, views along the section lines 8—8, 9—9, 10—10, and 11—11 of FIG. 7; and FIG. 12 is a sectional view of a screw fastening of FIG. 1 along the lines 12—12 of FIG. 1.

DETAILED DESCRIPTION

Figure 1:
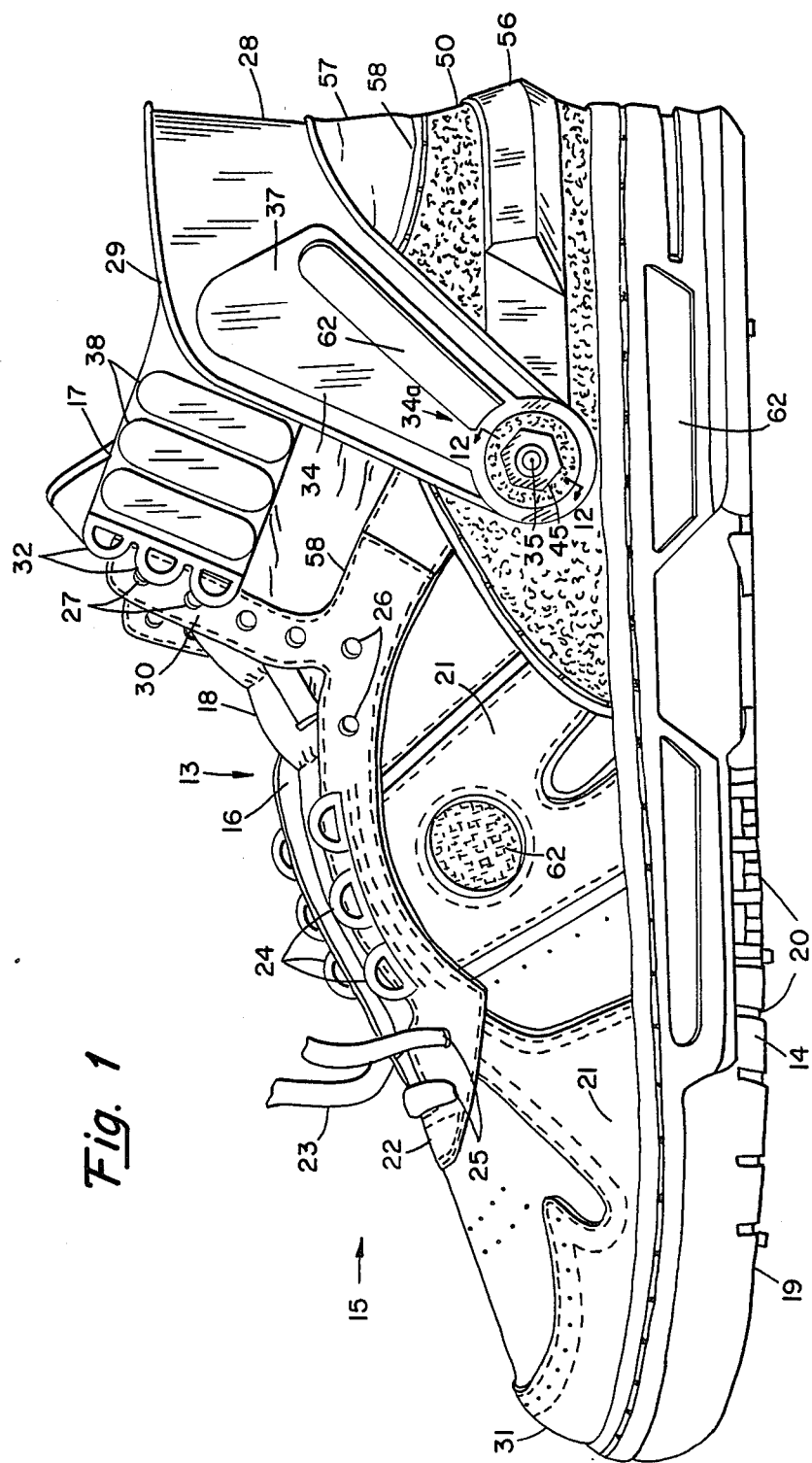
FIG. 1 is a side view of a shoe embodying the invention with attached exterior stabilizer means.

Referring to the figures, an athletic shoe 13 comprises a sole 14, an upper 15 attached to the sole 14 to enclose the foot, and a front opening 16 from low in front to the top of the upper to permit entry of the foot. A tongue 18 fills the opening 16 from below the opening 16 to above the top 17. The shoe may be lined in whole, or in part, (not shown) and may have a toe cap 31.

In this embodiment the athletic shoe 13 serves as a tennis shoe and has in the bottom 19 of the sole 14, a suitable pattern of indentations 20 to afford additional traction for the wearer. The sole 14 may be made of a resin based material. The upper 15 may be made of a real, synthetic or imitation leather, or all or part of canvas. An overlay 21 of leather which may also be real or imitation leather provides an attractive pattern and additional wear protection, as, for example, the pattern 22 at the edge of the opening 14 for the lacings 23 for closing the opening 16 over the tongue 18. The lacings 23 may be laced in customary fashion through lower openings or eyelets 25, thence through grommets 24, and thence through the two upper openings or eyelets 26 in the lower part of the upper 15, and thence through the openings or eyelets 27 in the top part of the upper 15 in a manner to be explained.

On the exterior of the shoe 13, an exterior stabilizer means 28 comprising a band or collar 29, compliant about the ankle but stiff vertically which encircles the ankle well above the malleoli. The collar 29 terminates at a front opening 30 and carries at the opening 30 grommets 32 for receiving the lacings 23. The grommets 32 on being laced register with the uppermost eyelets 27 of the shoe 13. A pair of stiff elements 34 extend vertically from pivot joints well below and a little back of the malleoli upwards to join the collar 29 with which the elements 34 are integral. In FIG. 7 half of the exterior stabilizer means 28 is shown, because these means are manufactured symmetrically about a center line 36 which then is a line vertically contained in the substantially vertical plane at the heel when the exterior stabilizer means are attached to the shoe 13 and laced. Slight thickening 37 of the vertical elements 34 in a vertical direction adds to their stiffness. Slightly thickened vertical plates 38 assist in stiffening the portions of the collar 29 forward of the elements 34. At the lower terminal end 34a of elements 34, a circular aperture 39 and a circular indented inner rim 40 of reduced thickness, both centered on a rotation axis 35 which are the pivot points. An externally threaded pin 45 having a knurled head 46 is partly countersunk in indented rim 40 when engaged in an internally threaded stem 47.

A molded stiff support 50 is fastened to part of the upper by stitching at the margins and also by adhesive, or the like, or both, extending about the heel and forward approximately to the instep on each side of the foot, thereby providing a stiff quarter for the shoe and protecting the achilles tendon and the heel bone. The support 50 is manufactured symmetrically about a center line indicated as the line 6—6 in FIG. 3 along which the section is taken, and thus FIG. 6 shows one-half of the support. Molded integrally with the support 50 is a raised circular portion 51 having a central axis 52. The post 47 is imbedded irrotationally in portion 51 by a spider 53, or the like, as by two wings 54, for example, which appear in FIG. 5. The rearmost portion of support 50 may be slightly lowered as at 55 for comfort of the achilles tendon. A thickened support plate 56 extends about the lower part of the quarter to near the malleoli. The support 50 and the support plate 56 strengthen the quarter and stiffen it to protect the achilles tendon and because the support 50 is also connected to pivot the stiff vertical elements 34 contributes to the protection against turning of the ankle. When the pins 45 are inserted and screwed into the stems 47 attaching the support 50 on each side, the pins 45 center the aperture 39 of the vertical stiffening member or elements 34, as they are slightly countersunk in indented inner rim 40 coaxially with axis 52 and 35 on each side. Even though the pin 40 is screwed tightly into stem 47, a light play admits of rotation of the exterior stabilizer elements 34 about these axis.

The top portion 57 of the upper 15 which lies under the collar 29 and against the ankle, when it is closed, that is, all above the line 58 is made of a soft, thicker material, fabric material to cushion the ankle against the closure of the collar 29. This top portion 57 somewhat wrinkles, as shown in FIG. 4 at 59, for example, when the collar 29 is drawn tight. The joining at 58 may be by stitching or adhesive, or both. The stitching in general of the different parts of the upper 15, and of the upper 15 to the sole 14, are not illustrated. Further, although the parts on each side of a central plane through the axis of the line 66 are symmetrical side to side in general, it will be understood that the sole 14 and the upper 15 are varied sufficiently in known manner, as in an arch support and shape of sole to distinguish and fit in comfort the left and right foot as required.

The seller's name or emblem, or other legend may appear as in raised format on the thickened support 56, or on other parts of the shoe as indicated at 62, in raised letter or otherwise.

The wearer may insert his foot into the shoe with the laces loose or unthreaded. The wearer then threads the laces criss-crossing in the usual manner up through eyelets 25, grommets 24, and eyelets 26. At the top three pairs of eyelets 27, and grommets 32, the laces pass in each case through the registering eyelet 27 and grommet 32. The wearer now pulls the laces tight and the collar 29 encircles the soft top portion 57 of the upper 15 (upper-most part). The stiff vertical elements 34 are of course pivoted about the pivot points, or pivots 52. Thus, the foot is encased in a manner generally to inhibit premature pronation, not only by virtue of the vertical elements 34 connected to the collar 29, but by the stiffness against turning of the collar itself, to which the stiffness of the stiffening braces or vertical plates 38 further contribute. When the wearer draws collar 29 tightly about the ankle, the vertical stiffness of the collar is enhanced because of its vertical dimension and because of its vertical stiffening plates 38. Further, the support 50 covers and protects the achilles tendon, and by its stiffness provides a stiff quarter that contributes to preventing twisting of the foot encased in this protective shoe, and tends to prevent rotation about a longitudinal axis of the foot though permitting usual rotation about a transverse axis. The shoe also affords the wearer an effective protection against injury to the ankle and foot. Although the shoe is designed and intended for use as a tennis shoe, its principles of construction may be employed in other footwear where premature pronation is to be prevented.

I claim:
1. An athletic shoe comprising:
   a sole;
   an upper attached to the sole and having an opening;
   a tongue to complete the opening;
   means for closing the opening about the foot; and
   exterior stabilizer means comprising a collar compliant about the ankle above the malleoli and stiff in the vertical direction, and a pair of stiff elements attached to and pivoted about pivot points of the shoe on opposite sides of the foot below the malleoli and each of the pair extending upwards from the pivot points to join the collar, said collar being tightened and joined at the front by said closing means.

2. An athletic shoe as claimed in claim 1, the pivot being about an axis substantially horizontal and parallel to the horizontal axis of the malleoli.

3. An athletic shoe as claimed in claim 2, the collar encircling also the upper, the closing means closing both the opening of the upper and the collar.

4. An athletic shoe as claimed in claim 1, the closing means comprising lacing.

5. An athletic shoe as claimed in claim 2, the collar encircling also the upper, the closing means comprising lacing, the same lacing closing both the collar and the opening of the upper.

6. An athletic shoe as claimed in claim 5, the collar and the upper having respectively matching grommets and eyelets respectively through which the lacing is threaded as the closing means.

7. An athletic shoe as claimed in claim 6, the shoe having a stiff support from the heel to the mid-sole on both sides of the shoe, to provide a stiff quarter contributing to the stiffness of the supporting means.

8. An athletic shoe as claimed in claim 7, the stiff support further comprising a support plate enchancing the support means.

* * * * *